United States Patent
Gualandi et al.

(10) Patent No.: US 10,125,190 B2
(45) Date of Patent: Nov. 13, 2018

(54) ANTI-COLLAGEN ANTIBODIES FOR TREATMENT AND DIAGNOSIS

(71) Applicant: Philogen S.P.A., Siena (IT)

(72) Inventors: Laura Gualandi, Zurich (CH); Rajesh Kamath, Southborough, MA (US); Annette Schwartz Sterman, Princeton, MA (US)

(73) Assignee: Philogen S.P.A., Siena (IT)

( * ) Notice: Subject to any disclaimer, the term of this patent is extended or adjusted under 35 U.S.C. 154(b) by 0 days.

(21) Appl. No.: 15/329,222

(22) PCT Filed: Jul. 28, 2015

(86) PCT No.: PCT/EP2015/067314
§ 371 (c)(1),
(2) Date: Jan. 25, 2017

(87) PCT Pub. No.: WO2016/016269
PCT Pub. Date: Feb. 4, 2016

(65) Prior Publication Data
US 2017/0226196 A1    Aug. 10, 2017

(30) Foreign Application Priority Data

Jul. 28, 2014 (GB) .................................. 1413357.3

(51) Int. Cl.
*A61K 39/395* (2006.01)
*C07K 16/18* (2006.01)
*A61K 47/48* (2006.01)
*A61K 49/00* (2006.01)

(52) U.S. Cl.
CPC ........ *C07K 16/18* (2013.01); *A61K 47/48538* (2013.01); *A61K 49/0004* (2013.01); *C07K 2317/565* (2013.01)

(58) Field of Classification Search
CPC .......... A61K 47/48538; A61K 49/0004; C07K 16/18; C07K 2317/565
See application file for complete search history.

(56) References Cited

FOREIGN PATENT DOCUMENTS

| EP | 2479190 | 7/2012 |
|---|---|---|
| WO | WO 94/18563 | 8/1994 |
| WO | WO 00/40597 | 7/2000 |
| WO | WO 2008/135734 | 11/2008 |
| WO | WO 2012/047583 | 4/2012 |

OTHER PUBLICATIONS

Ruszczak et al. Collagen as a carrier for on-site delivery of antibacterial drugs. Advanced Drug Delivery Reviews 55 (2003) 1679-1698 (Year: 2003).*
Man et al. Osteoarthritis pathogenesis—a complex process that involves the entire joint. Journal of Medicine and Life vol. 7, Issue 1, Jan.-Mar. 2014, pp. 37-41 (Year: 2014).*
Yoo et al. Type II Collagen Autoimmunity in Otosclerosis and Meniere's Disease. Science 217 (4565), 1153-1155., 1982 (Year: 1982).*
Amirahmadi et al., "An arthritogenic monoclonal antibody to type II collagen, CII-C1, impairs cartilage formation by cultured chondrocytes," *Immunology and Cell Biology*, vol. 82, pp. 427-434, 2004.
Burkhardt et al., "Epitope-Specific Recognition of Type II Collagen by Rheumatoid Arthritis Antibodies is Shared with Recognition in Antibodies That are Arthritogenic in Collagen-Induced Arthritis in the Mouse," *Arthritis & Rheumatism*, vol. 46, No. 9, pp. 2339-2348, 2002.
Chaudhary et al., "A human monoclonal antibody against the collagen type IV α3NC1 domain is a non-invasive optical biomarker for glomerular diseases," *Kidney International*, vol. 84, No. 2, pp. 403-408, 2013.
Cretu et al., "Disruption of endothelial cell interactions with the novel HU177 cryptic collagen epitope inhibits angiogenesis," *Clinical Cancer Research*, vol. 13, No. 10, pp. 3068-3078, 2007.
Dodge et al., "Immunohistochemical Detection and Immunochemical Analysis of Type II Collagen Degradation in Human Normal, Rheumatoid, and Osteoarthritic Articular Cartilages and in Explants of Bovine Articular Cartilage Cultured with Interleukin 1," *Journal of Clinical Investigation*, vol. 83, No. 2, pp. 647-661, 1989.
Freimark et al., "Targeting of humanized antibody D93 to sites of angiogenesis and tumor growth by binding to multiple epitopes on denatured collagens," *Molecular Immunology*, vol. 44, No. 15, pp. 3741-3750, 2007.
Hulmes, D. J. S., "Collagen Diversity, Synthesis and Assembly," in *Collagen: Structure and Mechanics*, Springer, pp. 15-47, 2008.
Nandakumar et al., "Efficient promotion of collagen antibody induced arthritis (CAIA) using four monoclonal antibodies specific for the major epitopes recognized in both collagen induced arthritis and rheumatoid arthritis," *Journal of Immunological Methods*, vol. 304, Nos. 1-2, pp. 126-136, 2005.
Weber et al., "A Highly Functional Synthetic Phage Display Library Containing over 40 Billion Human Antibody Clones," *PLoS One*, vol. 9, No. 6, e100000, 2014 (9 pages).
Xu et al., "Generation of monoclonal antibodies to cryptic collagen sites by using subtractive immunization," *Hybridoma*, vol. 19, No. 5, pp. 375-385, 2000.

* cited by examiner

*Primary Examiner* — Maher M Haddad
(74) *Attorney, Agent, or Firm* — Klarquist Sparkman, LLP

(57) ABSTRACT

The invention relates to the diagnosis and treatment of diseases, including cancer and inflammatory disorders. The invention provides, and involves the use of, antibodies that bind collagen.

15 Claims, 5 Drawing Sheets
Specification includes a Sequence Listing.

Cartilage Lateral Side     Cartilage Medial Side     Synovium

|  |  | 0.3 µg | 3 µg | 30 µg |
|---|---|---|---|---|
| Lesion cartilage | Incidence | 0/3 | 2/3 | 3/3 |
|  | IHC Score |  | 1+ | 1-3+ |
| Non-lesion cartilage | Incidence | 0/3 | 2/3 | 3/3 |
|  | IHC Score |  | 1-3+ | 4+ |
| Joint capsule | Incidence | 0/3 | 2/3 | 3/3 |
|  | IHC Score |  | 1+ | 2+ |

Cartilage Lateral Side    Cartilage Medial Side    Synovium

|  |  | 0.3 µg | 3 µg | 30 µg |
|---|---|---|---|---|
| Lesion cartilage | Incidence | 1/3 | 2/3 | 3/3 |
|  | IHC Score | 1+ | 1-3+ | 3-4+ |
| Non-lesion cartilage | Incidence | 1/3 | 2/3 | 3/3 |
|  | IHC Score | 1+ | 2+ | 3+ |
| Joint capsule | Incidence | 1/3 | 2/3 | 3/3 |
|  | IHC Score |  | 1+ | 3+ |

US 10,125,190 B2

ANTI-COLLAGEN ANTIBODIES FOR TREATMENT AND DIAGNOSIS

CROSS REFERENCE TO RELATED APPLICATION

This is the § 371 U.S. National Stage of International Application No. PCT/EP2015/067314, filed Jul. 28, 2015, which was published in English under PCT Article 21(2), which in turn claims the benefit of GB Application No. 1413357.3, filed Jul. 28, 2014, which is incorporated by reference herein in its entirety.

FIELD OF THE INVENTION

The present invention relates to the diagnosis and treatment of diseases, including cancer and inflammatory disorders. The invention provides, and involves the use of, antibodies that bind collagen.

BACKGROUND TO THE INVENTION

Most conventional pharmaceuticals currently in use for the treatment of serious disorders such as cancer and inflammatory diseases do not selectively accumulate at the site of disease [Bosslet et al., 58, 1195-1201 Cancer Res. (1998)]. For example, intravenously administered drugs distribute evenly within the different organs and tissues of the body, rather than selectively accumulating at the site of disease.

One approach to circumvent the disadvantages of conventional pharmacological therapies involves the preferential delivery of a bioactive agent to the site of disease by means of a binding molecule specific for a pathology-associated marker [Neri & Bicknell (2005), 5, 436-446 Nature Rev. Cancer]. The selective targeting of the drug to the diseased tissue will ultimately result in an increased local concentration at its site of action, sparing normal organs from the unwanted effects of the bioactive agent used to confer a pharmacological benefit (e.g., a growth factor, an enzyme, a hormone, an anti-inflammatory drug, a cytotoxic drug, a cytokine, a radionuclide, a photosensitizer). In most cases, this will lead to an improved therapeutic index of the delivered pharmaceutical, i.e. a higher efficacy with minimized side effects. Indeed, the favourable toxicity profile of site-specific therapeutics may open new avenues in the therapy of angiogenesis-related diseases, allowing the systemic administration of highly potent and promising agents, which are currently either given at suboptimal doses or whose clinical application has to date been impeded by unacceptable side-effects when applied in an unmodified form.

Ligand-based pharmacodelivery strategies fundamentally rely on the identification of good-quality markers of pathology, allowing a clear-cut discrimination between diseased tissues and healthy organs. Monoclonal antibodies and their fragments represent the preferred agents for pharmacodelivery applications [Rybak et al. 2, 22-40 Chem. Med. Chem (2007); Shrama et al., 5, 147-159 Nat. Rev. Drug Discovery (2006)], but globular protein mutants [Binz and Plückthun, 23, 1257-1268 Nature Biotechnology (2005)], peptides [Sergeeva et al., 58, 1622-1654, Adv. Drug. Deliv. Rev. (2006)] and even small organic ligands [Low et al., 41, 120-129, Acc. Chem. Res. (2008)] are also increasingly being used.

Antibody-based targeted delivery of bioactive agents to sites of angiogenesis as a therapeutic strategy for cancer treatment has been described. In the case of inflammatory disorders, antibody-based targeted delivery is much less well studied. The applicant has previously demonstrated that the ED-A domain of fibronectin, and the ED-B domain of fibronectin, two marker of angiogenesis, are expressed in the arthritic paws in the collagen-induced mouse model of rheumatoid arthritis. Using both radioactive and fluorescent techniques, the human monoclonal antibody F8, specific to ED-A, and the human monoclonal antibody L19, specific to ED-B, were found to selectively localize at sites of inflammation in vivo, following intravenous administration. When such antibodies were fused to the anti-inflammatory cytokine interleukin-10 the conjugate strong therapeutic activity was also shown (PCT/EP2007/004044, PCT/EP2008/009070). Nevertheless there remains a need in the art for further antibodies which can be employed in ligand-based pharmacodelivery applications for the treatment and diagnosis of diseases, such as cancer and inflammatory disorders.

Collagen

Collagens are the major structural components of the extracellular matrix. A coordinated and regulated expression of the different collagens is important for correct development in vertebrates and collagen mutations are involved in several inherited connective tissue disorders. Among them, Collagen type II (COL2A1) is the most abundant in cartilage [Strom C. M and Upholt W. B., Nuc Acid Res (1984), 12, 1025-1038 and Cheah K. S. et al., (1985) Biochem J, 229, 287-303]. COL2A1 is synthetized by chondrocytes during embryogenesis and de novo in pathological conditions in the adult. COL2A1 is a homotrimer composed of three α1(II) chains. These are secreted as long immature procollagen molecules that undergo proteolytic cleavage by collagenases in the extracellular environment, thereby forming the mature type II Collagen. COL2A1 forms heteropolymers with Collagen IX and Collagen XI, creating the fibrillar network typical of cartilage [Eyre D., (2002) Arthritis Res, 4, 30-35]. It has been known since the late 1980s that mutations in the COL2A1 gene are the cause of several hereditary disorders related to the abnormal development of bones and cartilage, including spondyloepiphyseal dysplasia congenital type [Lee B. et al., Science (1989), 244, 978-980], spondyloepimetaphyseal dysplasia strudwick type and many others.

Moreover different techniques have been used to investigate the expression of COL2A1 in normal and rheumatoid human articular cartilage. Normal COL2A1 is expressed evenly in healthy tissue, while diseased joints show strong enhancement of type II collagen [Aigner T. et al., (1992) Virchows Archives B Cell Pathol Incl Mol Pathol, 62, 337-345]. This evident change in the extracellular matrix composition is due to a failure of maintaining the homeostasis of the cartilage fibrillar network [Gouttenoire J. et al., (2004) Biorheology, 41, 535-542]. COL2A1 is reasonably well conserved between mouse, rat and man.

SUMMARY OF THE INVENTION

The present invention relates to the provision of novel antibody molecules for use in therapeutic and/or diagnostic applications. In particular, the antibody molecules of the present invention find use in pharmacodelivery applications.

Specifically, the present inventors have isolated novel antibody molecules which bind collagen, and have shown that these antibody molecules are capable of targeting vascular structures, including the neovasculature of tumour tissues and neovasculature associated with inflammatory disorders, such as rheumatoid arthritis (RA). These antibody molecules can thus be used for the targeted delivery of therapeutic and/or diagnostic agents to the neovasculature for which there is a continued need.

In a first aspect, the present invention relates to an antibody molecule that binds to collagen. The antibody may bind to collagen type II and, optionally, to collagen type I. Preferably, the antibody binds to collagen type II. Most preferably, the antibody binds to collagen type II alpha 1 (COL2A1). The collagen is preferably human collagen. The antibody molecule may comprise the HCDR3 of the C11 antibody molecule set forth in SEQ ID NO: 5, or an HCDR3 with the amino acid sequence set forth in SEQ ID NO: 5 with three or fewer amino acid substitutions, deletions, or insertions. In addition, the antibody molecule may comprise the HCDR1, HCDR2, LCDR1, LCDR2, and/or LCDR3 sequences of the C11 antibody molecule set forth in SEQ ID NOs 3-4 and 6-8. For example, the antibody molecule may comprise the VH domain and/or VL domain of the C11 antibody molecule set forth in SEQ ID NOs 1 and 2, respectively. Alternatively, the antibody molecule may comprise the HCDR3 of antibody molecule F9 set forth in SEQ ID NO: 13, or an HCDR3 with the amino acid sequence set forth in SEQ ID NO: 13 with three or fewer amino acid substitutions, deletions, or insertions. In addition, the antibody molecule may comprise the HCDR1, HCDR2, LCDR1, LCDR2, and/or LCDR3 sequences of the F9 antibody molecule set forth in SEQ ID NOs 11-12 and 14-16. For example, the antibody molecule may comprise the VH domain and/or VL domain of the F9 antibody molecule set forth in SEQ ID NOs 9 and 10, respectively.

As mentioned above, an antibody molecule of the invention may comprise a HCDR3 sequence as disclosed herein with three or fewer amino acid substitutions, deletions, or insertions. For example, an antibody molecule of the invention may comprise a HCDR3 sequence as disclosed herein with two or fewer, or one, amino acid substitution(s), deletion(s), or insertion(s). As with regard to the HCDR3 sequences, an antibody molecule of the invention may comprise a HCDR1, HCDR2, LCDR1, LCDR2, and/or LCDR3 sequence, as disclosed herein, with three or fewer, two or fewer, or one, amino acid substitution(s), deletion(s), or insertion(s). Similarly, and antibody molecule of the invention may comprise a VH and/or VL domain sequence as disclosed with ten or fewer, e.g. nine or fewer, eight or fewer, seven or fewer, six or fewer, five or fewer, four or fewer, three or fewer, two or fewer, or one, amino acid substitution(s), deletion(s), or insertion(s).

An antibody molecule, as referred to herein, may be in any suitable format. Many antibody molecule formats are known in the art and include both complete antibody molecule molecules, such as IgG, as well as antibody molecule fragments, such as a single chain Fv (scFv). The term "antibody molecule" as used herein encompasses both complete antibody molecule molecules and antibody molecule fragments, in particular antigen-binding fragments. Preferably, an antibody molecule comprises a VH domain and a VL domain. In a preferred embodiment, the antibody molecule is or comprises a scFv, is a small immunoprotein (SIP), is a diabody, or is a (complete) IgG molecule.

An antibody molecule of the present invention may be conjugated to a molecule to provide a conjugate. The choice of molecule conjugated to the antibody molecule will depend on the intended application of the conjugate. For example, where the conjugate is intended for the treatment of a disease or disorder, the conjugate may comprise an antibody molecule of the invention and a biocidal molecule, a cytotoxic molecule, a radioisotope, a photosensitizer, an enzyme, a hormone, an anti-inflammatory agent, or a cytokine. Where the conjugate is intended for use in imaging, detecting, or diagnosing a disease or disorder, the conjugate may comprise an antibody molecule of the invention and a detectable label, such as a radioisotope, e.g. a non-therapeutic radioisotope. Depending on the molecule conjugated to the antibody molecule, the conjugate may be or may comprise a single chain protein. When the conjugate is a single chain protein, the entire protein can be expressed as a single polypeptide or fusion protein. In this case, the molecule may be conjugated to the antibody molecule by means of a peptide linker. Fusion proteins have the advantage of being easier to produce and purify since they consist of one single species. This facilitates production of clinical-grade material. Alternatively, the molecule may be conjugated to the antibody molecule by means of a cleavable linker.

The invention also provides isolated nucleic acids encoding the antibodies and conjugates of the invention. The skilled person would have no difficulty in preparing such nucleic acids using methods well-known in the art. An isolated nucleic acid may be used to express the antibody molecule or conjugate of the invention, for example by expression in a bacterial, yeast, insect or mammalian host cell. A preferred host cell is *E. coli*. The nucleic acid will generally be provided in the form of a recombinant vector for expression. Host cells in vitro comprising such vectors are part of the invention, as is their use for expressing the antibodies and conjugates of the invention, which may subsequently be purified from cell culture and optionally formulated into a pharmaceutical composition.

An antibody molecule or conjugate of the invention may be provided for example in a pharmaceutical composition, and may be employed for medical use as described herein, either alone or in combination with one or more further therapeutic agents. Alternatively, the antibody molecule or conjugate of the invention may be provided in a diagnostic composition and may be employed for diagnostic use as described herein.

In a second aspect, the invention relates to an antibody molecule or conjugate of the invention for use in a method for treatment of the human or animal body by therapy. For example, an antibody molecule or conjugate of the invention may for use in a method of treating an inflammatory disorder, inhibiting angiogenesis, treating cancer, and/or treating an autoimmune disease in a patient. The invention also relates to a method of treating an inflammatory disorder, inhibiting angiogenesis, treating cancer, and/or treating an autoimmune disease in a patient, the method comprising administering a therapeutically effective amount of an antibody molecule or conjugate of the invention to the patient.

In a third aspect, the invention relates to an antibody molecule of the invention for use in a method of delivering a molecule to sites of an inflammatory disorder, sites of neovasculature which are the result of angiogenesis, sites of cancer and/or sites of autoimmune disease in a patient. The invention also relates to a method of delivering a molecule to sites of an inflammatory disorder, sites of neovasculature which are the result of angiogenesis, sites of cancer and/or sites of autoimmune disease in a patient comprising administering to the patient an antibody molecule of the invention, wherein the antibody molecule is conjugated to the molecule.

In a fourth aspect, the invention relates to an antibody molecule or conjugate of the invention for use in a method of imaging, detecting, or diagnosing an inflammatory disorder, angiogenesis, cancer, and/or an autoimmune disease in a patient. The invention further relates to a method of imaging, detecting, or diagnosing an inflammatory disorder, angiogenesis, cancer, and/or an autoimmune disease in a patient comprising administering an antibody molecule or conjugate of the invention to the patient.

A patient, as referred to herein, is preferably a human patient.

DETAILED DESCRIPTION

Figure 1:
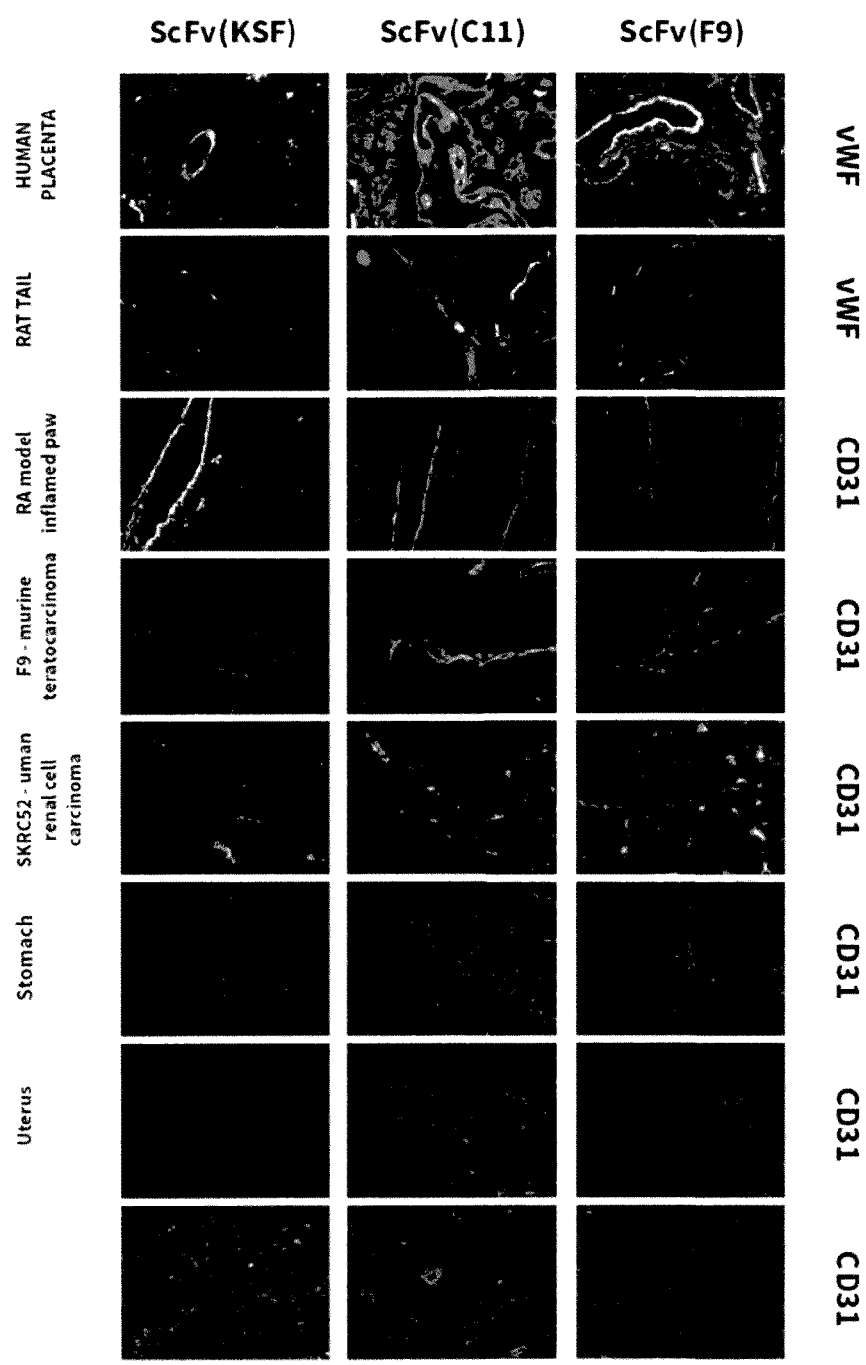
FIG. 1 shows that anti-collagen antibodies C11 and F9 are capable of staining vascular structures in different tissues (as indicated). No staining was observed with the control antibody scFv(KSF) which is specific for hen egg lysozyme. Antibodies specific for von Willebrand factor (vWF) or CD31 were used as endothelial markers.

The invention includes the combination of the aspects and preferred features described except where such a combination is clearly impermissible or expressly avoided.

The present invention relates to an antibody which binds collagen.

Antibody Molecule

The term "antibody molecule" describes an immunoglobulin whether natural or partly or wholly synthetically produced. The term also covers any polypeptide or protein having a binding domain which is, or is substantially homologous to, an antibody binding domain. Examples of antibodies are the immunoglobulin isotypes and their isotypic subclasses; fragments which comprise an antigen binding domain such single chain diabodies. The antibody molecule or fragment thereof may be human or humanised. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

The term "specific" may be used to refer to the situation in which the antibody molecule will not show any significant binding to molecules other than its specific binding partner(s). The term is also applicable where e.g. an antigen-binding site of an antibody molecule is specific for a particular epitope that is carried by a number of antigens, in which case the antibody molecule carrying the antigen-binding site will be able to bind to the various antigens carrying the epitope.

The antibody molecule may be monovalent or bivalent i.e. may have two antigen binding sites. Where the antibody molecule is bivalent, the two antigen binding sites may be identical or different. An "antigen binding site" describes the part of an antibody which comprises the area which specifically binds to and is complementary to part or all of an antigen. Where an antigen is large, an antibody molecule may only bind to a particular part of the antigen, which part is termed an epitope. An antigen binding site may be provided by one or more antibody variable domains (e.g. a so-called Fd antibody fragment consisting of a VH domain).

Preferably, an antigen binding site comprises an antibody light chain variable region (VL) and an antibody heavy chain variable region (VH).

An antibody molecule of the invention preferably comprises the HCDR3 antibody C11, or antibody F9. The HCDR3 is known to play a role in determining the specificity of an antibody molecule (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144: 4863-4869; Kabat et al., (1991b), J. Immunol., 147:1709-1719).

The antibody molecule may further comprise the HCDR1, HCDR2, LCDR1, LCDR2 and/or LCDR3 of antibody antibody C11, or antibody F9.

The antibody may also comprise the VH and/or VL domain of antibody antibody C11, or antibody F9.

An antibody molecule of the invention may have a VH domain having at least 70%, more preferably one of at least 75%, 80%, 85%, 90%, 95%, 96%, 97%, 98%, 99% or 100%, sequence identity to the VH domain of antibody antibody C11, or antibody F9.

An antibody molecule of the invention may have a VL domain having at least 70%, more preferably one of at least 75%, 80%, 85%, 90%, 95%, 96%, 97%, 98%, 99% or 100%, sequence identity to the VL domain of antibody antibody C11, or antibody F9.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Variants of these VH and VL domains and CDRs may also be employed in antibody molecules for use in as described herein. Suitable variants can be obtained by means of methods of sequence alteration, or mutation, and screening.

Particular variants for use as described herein may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1.

Alterations may be made in one or more framework regions and/or one or more CDRs. In particular, alterations may be made in HCDR1, HCDR2 and/or HCDR3.

The antibody molecule may be a whole antibody or a fragment thereof, in particular an antigen-binding fragment thereof.

Whole antibodies include IgA, IgD, IgE, IgG or IgM. Preferably, the whole antibody is IgG.

Antigen-binding fragments of whole antibodies include (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO2013/014149; WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

A single chain Fv (scFv) may be comprised within a mini-immunoglobulin or small immunoprotein (SIP), e.g. as described in (Li et al., (1997), Protein Engineering, 10: 731-736). An SIP may comprise an scFv molecule fused to the CH4 domain of the human IgE secretory isoform IgE-S2 ($\varepsilon_{S2}$-CH4; Batista et al., (1996), J. Exp. Med., 184: 2197-205) forming an homo-dimeric mini-immunoglobulin antibody molecule Preferably the antibody molecule comprises or consists of a single chain Fv, a small immunoprotein, a diabody, or a (whole) IgG molecule.

Conjugates

Conjugates of the invention comprise an antibody molecule of the invention and a therapeutic or diagnostic agent. The therapeutic agent may be a biocidal molecule, a cytotoxic molecule, a radioisotope, a photosensitizer, an enzyme, a hormone, or an anti-inflammatory agent. Preferably, the therapeutic agent is a biocidal molecule, a cytotoxic molecule, a radioisotope, or an anti-inflammatory agent. The biocidal molecule, cytotoxic molecule, or anti-inflammatory agent may be a cytokine.

The diagnostic agent may be radioisotope, e.g. a non-therapeutic radioisotope.

Radioisotopes which may be conjugated to a binding member of the invention include isotopes such as $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{123}$I, $^{124}$I, $^{125}$I, $^{131}$I, $^{18}$F, $^{211}$At and $^{225}$Ac. Preferably, positron emitters, such as $^{18}$F and $^{124}$I, or gamma emitters, such as $^{99m}$Tc, $^{111}$In and $^{123}$I, are used for diagnostic applications (e.g. for PET), while beta-emitters, such as $^{131}$I, $^{90}$Y and $^{177}$Lu, are preferably used for therapeutic applications. Alpha-emitters, such as $^{211}$At and $^{225}$Ac may also be used for therapy. In one example, the specific binding member may be conjugated to $^{177}$Lu or $^{90}$Y.

The specific binding member may be conjugated with the therapeutic agent by means of a peptide bond or linker, i.e. within a fusion polypeptide comprising said molecule and the specific binding member or a polypeptide chain component thereof. Other means for conjugation include chemical conjugation, especially cross-linking using a bifunctional reagent (e.g. employing DOUBLE-REAGENTS™ Cross-linking Reagents Selection Guide, Pierce).

Linkers

The antibody molecule and the therapeutic or diagnostic agent may be connected to each other directly, for example through any suitable chemical bond or through a linker, for example a peptide linker.

The peptide linker may be a short (2-20, preferably 2-15, residue stretch of amino acids). Suitable examples of peptide linker sequences are known in the art. One or more different linkers may be used. The linker may be about 5 amino acids in length.

The chemical bond may be, for example, a covalent or ionic bond. Examples of covalent bonds include peptide bonds (amide bonds) and disulphide bonds. For example the antibody molecule and therapeutic or diagnostic agent may be covalently linked. For example by peptide bonds (amide bonds). Thus, the antibody molecule and therapeutic or diagnostic agent may be produced (secreted) as a single chain polypeptide. The individual components that form the antibody molecule or the therapeutic or diagnostic agent may also be connected directly, for example through any suitable chemical bond, or through a linker, for example a peptide linker. Examples of individual components which may be linked within the antibody molecule are CDRs or VH or VL sequences.

Methods of Treatment and Diagnosis

An antibody molecule or conjugate of the invention may be used in a method of treatment of the human or animal body, such as a method of treatment (which may include prophylactic treatment) of a disease or disorder in a patient (typically a human patient) comprising administering the antibody molecule or conjugate to the patient.

Accordingly, such aspects of the invention provide methods of treatment comprising administering an antibody molecule or conjugate of the invention, pharmaceutical compositions comprising such an antibody molecule or conjugate for the treatment of a condition or disease, and a method of making a medicament or pharmaceutical composition comprising formulating the antibody molecule or conjugate of the present invention with a physiologically acceptable carrier or excipient.

An antibody molecule or conjugate as herein described may be used in a method of treating an inflammatory disorder, inhibiting angiogenesis, treating cancer, and/or treating an autoimmune disease in a patient. The method may comprise targeting a therapeutic agent to the neovasculature in vivo. The agent may be any therapeutic agent discussed herein, which is suitable for treatment of the disease or disorder in question.

Also contemplated is a method of treating an inflammatory disorder, inhibiting angiogenesis, treating cancer, and/or treating an autoimmune disease in a patient by targeting a therapeutic agent to the neovasculature in a patient, the method comprising administering a therapeutically effective amount of an antibody molecule or conjugate as herein described to the patient.

An antibody molecule or conjugate as herein described may also be used in a method of imaging, detecting, or diagnosing a disease or disorder in a patient. A method of imaging, detecting, or diagnosing a disease or disorder comprising administering an antibody or conjugate as described herein to a patient is similarly contemplated. The disease or disorder may be an inflammatory disorder, angiogenesis, cancer, and/or an autoimmune disease. The method may comprise targeting a diagnostic agent, such as a detectable label, to the neovasculature in vivo.

Inflammatory disorders include any disease or disorder which is characterised by an inflammatory abnormality. Such disease include, for example, immune system disorders, such as autoimmune diseases, and cancer.

Angiogenesis is a feature of many known diseases and disorders and inhibition of angiogenesis using an antibody or conjugate of the invention may be used to treat such diseases and disorders. Similarly, diseases and disorders characterised by angiogenesis may be imaged, detected, or diagnosed using an antibody or conjugate described herein. Disease characterised by angiogenesis include, for example, rheumatoid arthritis, diabetic retinopathy, age-related muscular degeneration, angiomas, tumours and cancer.

As mentioned above, conditions which may be treated, imaged, detected, or diagnosed using an antibody or conjugate as described herein include cancer, as well as other tumours and neoplastic conditions.

Exemplary cancers include any type of solid or non-solid cancer or malignant lymphoma and especially liver cancer, lymphoma, leukaemia (e.g. acute myeloid leukaemia), sarcomas, skin cancer, bladder cancer, breast cancer, uterine cancer, ovarian cancer, prostate cancer, lung cancer, colorectal cancer, cervical cancer, head and neck cancer, oesophageal cancer, pancreatic cancer, renal cancer, stomach cancer and cerebral cancer. Cancers may be familial or sporadic. Cancers may be metastatic or non-metastatic. The cancer, tumour, or neoplastic condition preferably expresses collagen.

Autoimmune disease which may be treated, imaged, detected, or diagnosed using an antibody or conjugate as described herein include lupus erytematosus, rheumatoid arthritis, and psoriathic arthritis.

A further disease or disorder which may treated, imaged, detected, or diagnosed using an antibody or conjugate described herein is osteoarthritis.

Pharmaceutical Compositions

A further aspect of the present invention relates to a pharmaceutical composition comprising at least one antibody molecule or conjugate of the invention and optionally a pharmaceutically acceptable excipient.

Pharmaceutical compositions of the present invention typically comprise a therapeutically effective amount of an antibody molecule or conjugate according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilisers, antioxidants, pH-regulating substances, controlled-release excipients. The pharmaceutical composition of the invention may be adapted, for example, for parenteral use and may be administered to the patient in the form of solutions or the like.

Pharmaceutical compositions comprising the antibody molecule or conjugate of the present invention may be administered to a patient. Administration is preferably in a "therapeutically effective amount", this being sufficient to show benefit to the patient. Such benefit may be amelioration of at least one symptom. The actual amount administered, and rate and time-course of administration, will depend on the nature and severity of what is being treated. Prescription of treatment, e.g. decisions on dosage etc., is within the responsibility of general practitioners and other medical doctors. Treatments may be repeated at daily, twice-weekly, weekly, or monthly intervals at the discretion of the physician.

A pharmaceutical composition of the invention may be administered to a patient in need of treatment via any suitable route, usually by injection into the bloodstream and/or directly into the site to be treated. The precise dose and its frequency of administration will depend upon a number of factors, the route of treatment, the size and location of the area to be treated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included For intravenous injection, or injection at the site of affliction, the pharmaceutical composition will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A pharmaceutical composition may be administered alone or in combination with other treatments, either simultaneously or sequentially dependent upon the condition to be treated.

Kits

Another aspect of the invention provides a therapeutic kit for use in the treatment of a disease or disorder comprising an antibody molecule or conjugate as described herein. The components of a kit are preferably sterile and in sealed vials or other containers.

A kit may further comprise instructions for use of the components in a method described herein. The components of the kit may be comprised or packaged in a container, for example a bag, box, jar, tin or blister pack.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1—Preparation and Characterisation of Two New Antibodies Against Collagen The C11 and F9 antibodies were isolated in scFv configuration from phage display libraries as described by PCT/EP2009/006487 according to the screening technique described by Silacci et al. (Protein Engineering Design & Selection, 2006, 19, 471-478). For the generation of fully human monoclonal antibodies a commercial preparation of human type II collagen (Yo Proteins—Karolinska Institute Science Park, Cat. No. 210) was used. ScFv antibody fragments were expressed in *E. coli* TG-1 cells and purified from culture supernatant by affinity chromatography, using protein A resin (Sino Biological Inc.) Purified antibodies were analyzed by size-exclusion chromatographyon superdex 75 HR10/30 columns (Amersham Biosciences), peaks representing monomeric fractions were collected and used for affinity measurements by BIAcore on a low-density coated antigen chip.

Both antibodies C11 and F9 displayed good staining of vascular structures as revealed by immunofluorescence analysis of a number of different tissues and tumour samples (see FIG. 1). No staining was observed with the control antibody scFv(KSF) which is specific for hen egg lysozyme.

Figure 2B:
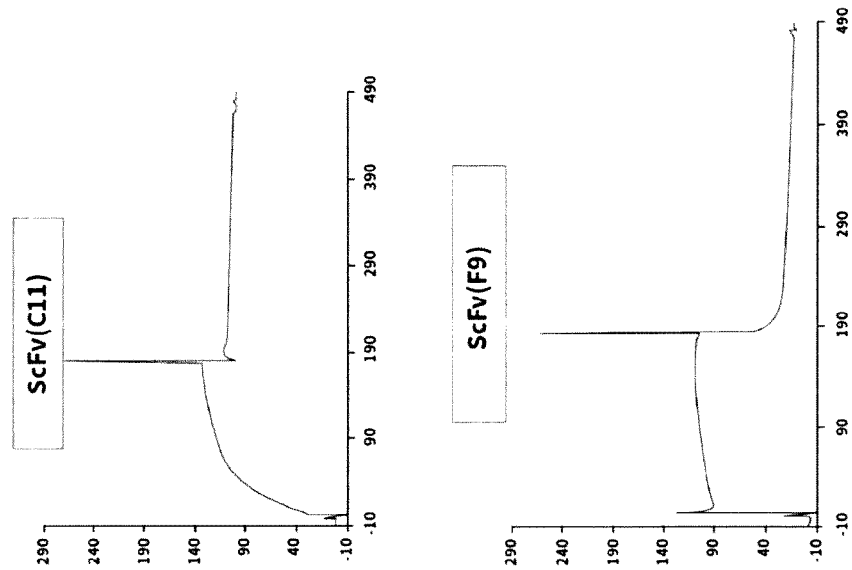
FIG. 2B shows Biacore data demonstrating binding of antibodies C11 and F9 to collagen type II.
Figure 2A:
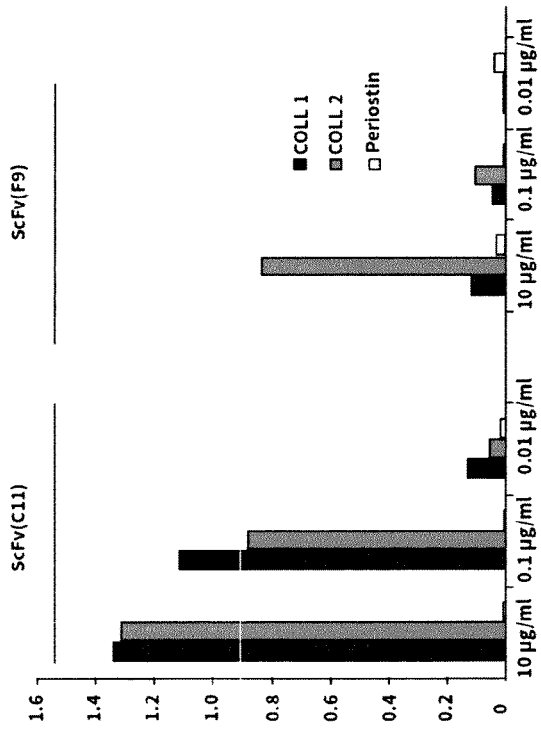
FIG. 2A shows the results of an ELISA which demonstrates that anti-collagen antibody F9 has a higher specificity for collagen type II than anti-collagen antibody C11, which recognizes both collagen type I and collagen type II. Periostin was used as negative control.

Characterisation by ELISA revealed that antibody F9 has a higher specificity for collagen type II than antibody C11, which recognizes both collagen type I and collagen type II as shown in FIG. 2A. Periostin was used as a negative control.

Binding of antibodies C11 and F9 to collagen type II was also confirmed by Biacore analysis. The results are shown in FIG. 2B.

Immunofluorescence Analysis:

Double staining for collagen type II and von Willebrand factor (vWF) or CD31, as endothelial markers, was performed on several specimens: human placenta, rat tail, mouse spleen, mouse uterus, mouse stomach, mouse paw from a RA model, xenograft tumor model (SKRC52) and a murine tumor model (F9 teratocarcinoma). The frozen specimens were sectioned at 10 µm thickness and treated with ice-cold acetone, rehydrated in PBS and blocked with 3% BSA. Affinity-purified scFv fragments (final concentration 5 mg/ml) carrying a myc-tag were added onto the sections followed by biotinylated monoclonal anti-myc antibody 9E10 antibody (5 mg/ml) and the endothelial marker antibody. Bound scFvs were detected with Strepavidin Alexa 594 (Molecular Probes), for the anti-vWF (DAKO) and anti-CD31 (BD Pharmingen) were used respectively goat anti-rabbit IgG Alexa 488 or goat ant-rat IgG Alexa 488. DAPI was used as nuclei staining. ScFv(KSF) anti-hen egg lysozyme was used as an isotype negative control for the staining.

ELISA:

MaxiSorp plates (NUNC) were coated with collagen type II (Yo Proteins), collagen type I (Chondrex) or an unrelated protein (periostin) at 20 µg/mL final concentration.

ScFv fragments were incubated for 1 hour, and bound antibody was detected with Protein A horse radish peroxidase (HRP) conjugate (GE Healthcare). The assay was developed by a colorimetric reaction using BM-Blue POD soluble substrate (Roche).

Biacore Analysis:

Monomeric fractions of antibodies C11 and F9 were analyzed by surface plasmon resonance (BIAcore, 3000 system). Human type II collagen was covalently coupled to the surface of the CM-3 sensor Chip. Thirty microliters of each sample were injected at the flow rate of 10 µL/min. The regeneration of the chip was performed with 5 µL of 10 mM HCl.

Example 2—Biodistribution Studies and IHC Analysis Using Anti-Collagen Antibodies Biodistribution of anti-collagen antibodies C11 and F9 was tested in a rat medial meniscus tear (MMT) model of osteoarthritis (OA). IHC analysis was performed on tissues from the rat MMT model and on cartilage from human tissue.

For the MMT model of OA, weight matched Lewis rats (300-325 g) were subjected to MMT surgery of the knee. The sham surgery was performed by exposing the joint and transecting the medial collateral ligament. In MMT animals the exposed meniscus was then transected at its narrowest point. The joint and skin were then closed with sutures. For the biodistribution studies only, rats were then injected intra-articularly in the knee with the targeting mAb (antibody C11 or F9) on day 17 and knee joints were harvested on day 20. The tibiae and femur, including the knee joint were harvested, dissected free of surrounding tissues and the tibiae were separated from the rest of the joint. The tissue was then fixed in 10% neutral buffered formalin for 3-4 days and decalcified in Cal-Ex II (Fisher Scientific, Waltham, Mass.) for 14 days. Dehydrated samples were embedded in paraffin using routine methods. Coronal sections were cut at 5 µm thickness.

Figures 3A, 3B:
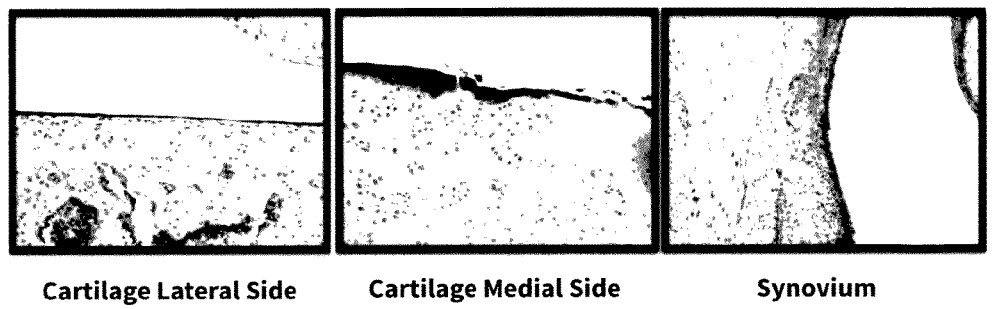
FIGS. 3A and C: Rats (n=3) were injected with either antibody C11 (30 µg) or F9 (30 µg) and knee joints harvested as described in the Examples. Immunodetection of antibodies C11 and F9 in coronal sections of the harvested knee joints showed staining of cartilage on the cartilage medial (disease) side of the joint and minimal to no staining on the cartilage lateral (non-disease) side of the joint (see FIGS. 3A and C, respectively). Interestingly with the C9 antibody minimal staining was observed of the underlying connective tissue in the synovium while F9 showed a strong staining of the underlying connective tissue in the synovium.
FIGS. 3B and D shows the results of a dose response bio-distribution study of anti-collagen antibodies C11 and F9, respectively, in a rat MMT model of osteoarthritis. Rats (n=3 per dose group) were injected with either antibody C11 (0.3, 3 and 30 µg) or F9 (0.3, 3 and 30 µg) and knee joints harvested as described in the Examples. IHC was performed as described for FIGS. 3A and C. Incidence in FIGS. 3B and D refers to the number of animals staining positive while IHC score refers to the intensity of staining with score=0 (no staining); score=1 (mild intensity staining); score=2 (moderate intensity staining) and score=3 (strong intensity staining). Both antibodies showed dose dependent incidence and intensity of staining indicating (1) that the signals observed in FIGS. 3A and C are reproducible at a 30 µg dose and (2) that the signal is specific to type II collagen, as signal incidence and intensity diminished in a dose dependent manner FIGS. 3B and D.
Figures 3C, 3D:
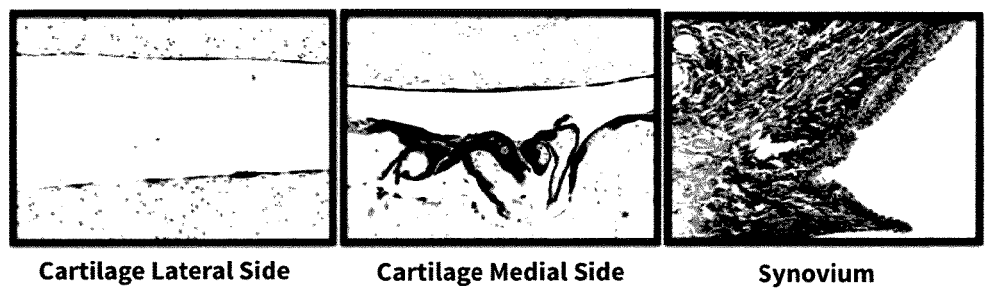
FIG. 3 shows the results of a bio-distribution study of anti-collagen antibodies C11 and F9 in a rat medial meniscus tear (MMT) model of osteoarthritis.

For IHC analysis of tissues from the biodistribution studies, all slides were treated with Vector streptavidin block for 15 minutes, Vector biotin block for 15 minutes, Dako Dual Endogenous Enzyme block for 10 minutes and Dako protein block for 20 minutes after epitope retrieval. Subsequent to blocking for endogenous enzyme activity and non-specific binding, Rabbit anti-human antibody at 2 ug/mL was incubated on slides for 30 minutes to detect the primary antibody (C11 or F9). Leica anti-rabbit HRP polymer was used to label the secondary antibody (10 minutes) followed by application of Leica Bond DAB Refine (diaminobenzidine) for 2 minutes to stain the reaction. Slides were counterstained with hematoxylin. Three wash steps with Leica wash buffer were performed between each step. The results are shown in FIG. 3.

Knee joint cartilage and synovium from human osteoarthritis patients was obtained from Asterand, Detroit, Mich. USA or NDRI, Philadelphia, Pa. USA. For IHC analysis of the human joint tissues, all slides were treated with Vector streptavidin block for 15 minutes, Vector biotin block for 15 minutes, Dako Dual Endogenous Enzyme block for 10 minutes and Dako protein block for 20 minutes after epitope retrieval. Subsequent to blocking for endogenous enzyme activity and non-specific binding, biotinylated C11 antibody at 0.3 µg/ml or biotinylated F9 antibody at 5.0 µg/ml (primary antibodies) were added to tissues and incubated for 60 minutes. Vector ABC Elite reagent (streptavidin-HRP) was used for 30 minutes to detect the primary antibody. Leica Bond DAB Refine (diaminobenzidine) was applied for 2 minutes to stain the reaction. Slides were counterstained with hematoxylin. Three wash steps with Leica wash buffer were performed between each step. The results are shown in FIG. 4.

For IHC analysis of rat OA knee joint tissues (Rat MMT model on day 21 after surgery to induce OA), the knee joints were harvested, dissected free of surrounding tissues and the tibiae were separated from the rest of the joint. The tissue was then fixed in 10% neutral buffered formalin for 3-4 days and decalcified in Cal-Ex II (Fisher Scientific, Waltham, Mass.) for 14 days. Dehydrated samples were embedded in paraffin using routine methods. Coronal sections were cut at 5 µm thickness. All slides were treated with Vector streptavidin block for 15 minutes, Vector biotin block for 15 minutes, Dako Dual Endogenous Enzyme block for 10 minutes and Dako protein block for 20 minutes after epitope retrieval. Subsequent to blocking for endogenous enzyme activity and non-specific binding, unlabeled human C11 antibody at 0.0075 µg/ml or unlabeled human F9 antibody at 0.027 µg/ml (primary antibodies) were added to the tissues and incubated 60 minutes. Rabbit anti-human antibody at 2 ug/mL was incubated on slides for 30 minutes to detect the primary antibody. Leica anti-rabbit HRP polymer was used to label the secondary antibody (10 minutes) followed by application of Leica Bond DAB Refine (diaminobenzidine) for 2 minutes to stain the reaction. Slides were counterstained with hematoxylin. Three wash steps with Leica wash buffer were performed between each step. The results are shown in FIG. 4.

In the rat MMT model of OA, joint damage (cartilage) is localized to the medial side while there is no damage on the lateral side of the joint, as disease is induced by tearing the medial meniscus. The F9 and C11 mAbs, which target type II collagen, showed staining of cartilage on the medial (disease) side of the joint and minimal to no staining on the lateral (non-disease) side of the joint (FIGS. 3A and C). This data demonstrates that the targeting mAb are retained in the disease (lesional) regions of the cartilage and not in non-disease (non-lesional) regions.

Figure 4A:
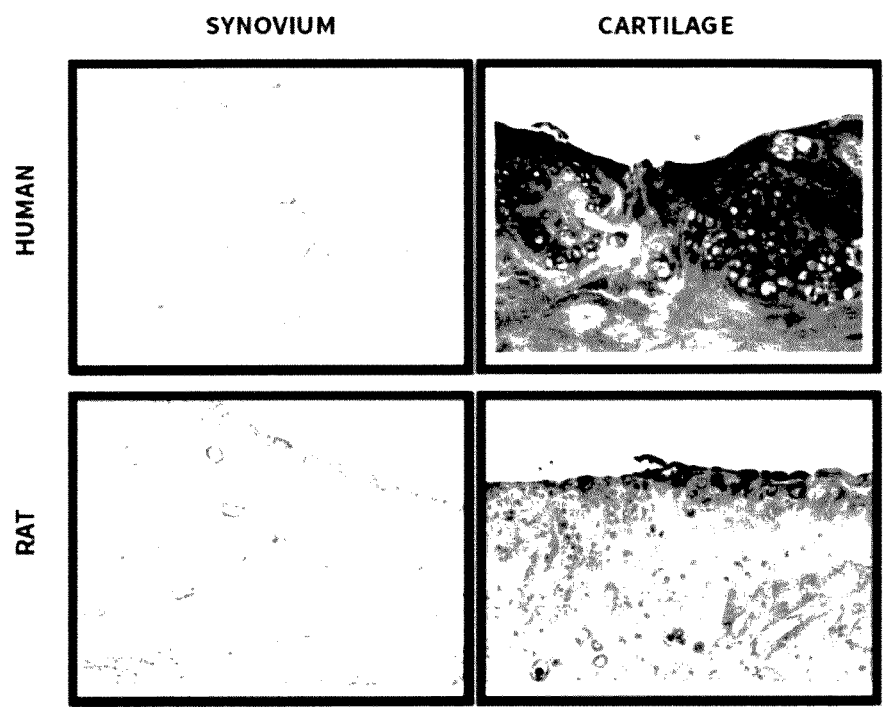
FIGS. 4A and B show the results of immunohistochemistry (IHC) studies performed on synovium and knee joint cartilage from human osteoarthritis patients obtained from Asterand, Detroit, Mich. USA (top two squares in FIGS. 4A and B) and coronal sections of knee joints from a rat medial meniscus tear (MMT) model of osteoarthritis (OA) (bottom two squares in FIGS. 4A and B). With antibody C11 (FIG. 4A), staining of chondrocytes and cartilage in both human and rat were observed in the IHC studies, as was the case in the bio-distribution studies reported in FIG. 3, and minimal intensity synovium and vascular staining was observed by IHC. In addition, IHC of knee joints showed staining of the subchondral bone in both human and rat samples. With antibody F9 (FIG. 4B), staining of synovium and cartilage observed by IHC was consistent between the human and rat samples and comparable with that observed in the biodistribution studies.
Figure 4B:
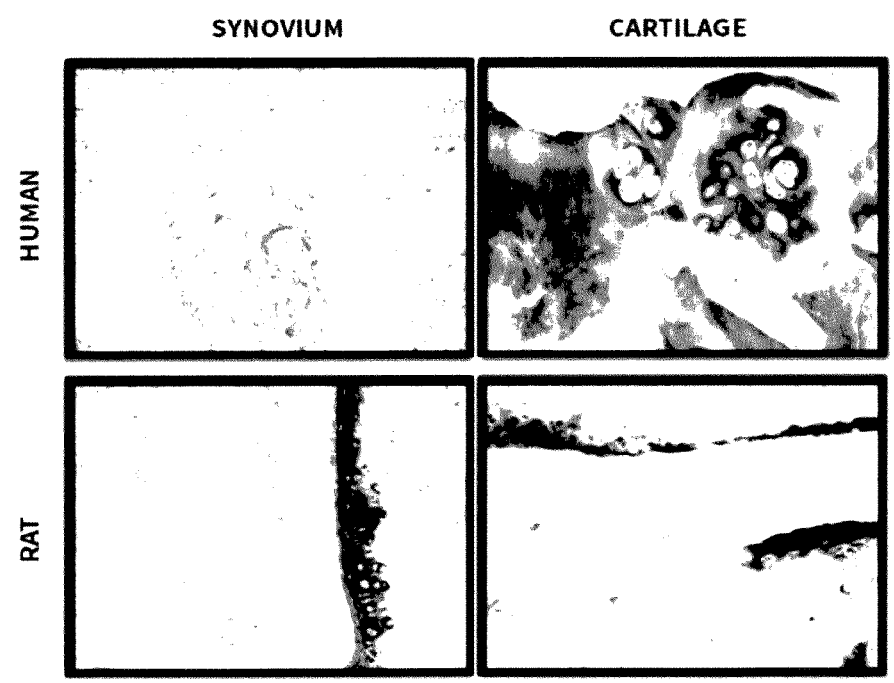

Antibody C11 showed staining of chondrocytes and cartilage in both human and rat in IHC studies, as was the case in the bio-distribution studies reported in FIG. 3, and minimal intensity synovium and vascular staining was observed by IHC. In addition, IHC of knee joints showed staining of the subchondral bone in both human and rat samples (FIG. 4A). With antibody F9 (FIG. 4B), staining of synovium and cartilage observed by IHC was consistent between the human and rat samples and comparable with that observed in the biodistribution studies reported in FIG. 3.

In summary, both anti-collagen antibodies, C11 and F9, target epitopes within the type II collagen protein (major protein of the extracellular matrix of cartilage) and have the potential to target therapeutics to osteoarthritic joints. The C11 antibody stained damaged cartilage and subchondral bone (subchondral bone staining was observed only in IHC of human and rat knee joints) with minimal synovium staining while the F9 antibody stained damaged cartilage and synovium in in vivo bio-distribution studies (FIG. 3) and IHC of human and rat OA knee joints (FIG. 4).

SEQUENCE LISTING

The Sequence Listing is submitted as an ASCII text file in the form of the file named Sequence_Listing.txt, which was created on Jan. 24, 2017, and is 7591 bytes, which is incorporated by reference herein.

Amino acid sequences of antibody C11 specific for collagen

SEQ ID NO: 1 (C11-VH)
EVQLLESGGGLVQPGGSLRLSCAASGFTFSSYAMSWVRQAPGKGLEQVS
AISGSGGSTYYADSVKGRFTISRDNSKNTLYLQMNSLRAEDTAVYYCAK
TLAAFDYWGQGTLVTVSS

SEQ ID NO: 2 (C11-VL)
EIVLTQSPGTLSLSPGERATLSCRASQSVSSSYLAWYQQKPGQAPRLLI
YGASSRATGIPDRFSGSGSGTDFTLTISRLEPEDFAVYYCQQAIGFPQT
FGQGTKVEIK

SEQ ID NO: 3 (C11-VH CDR1)
GFTFSSYAMS

SEQ ID NO: 4 (C11-VH CDR2)
AISGSGGSTYYADSVKG

SEQ ID NO: 5 (C11-VH CDR3)
TLAAFDY

SEQ ID NO: 6 (C11-VL CDR1)
RASQSVSSSYLA

-continued

SEQ ID NO: 7 (C11-VL CDR2)
GASSRAT

SEQ ID NO: 8 (C11-VL CDR3)
QQAIGFPQT

Amino acid sequences of antibody F9 specific for collagen

SEQ ID NO: 9 (F9-VH)
EVQLLESGGGLVQPGGSLRLSCAASGFTFSSYAMSWVRQAPGKGLEWVS
AISGSGGSTYYADSVKGRFTISRDNSKNTLYLQMNSLRAEDTAVYYCAK
AGYSLFDYWGQGTLVTVSS

SEQ ID NO: 10 (F9-VL)
EIVLTQSPGTLSLSPGERATLSCRASQSVSSSYLAWYQQKPGQAPRLLI
YGASSRATGIPDRFSGSGSGTDFTLTISRLEPEDFAVYYCQQDQGMPLT
FGQGTKVEIK

SEQ ID NO: 11 (F9-VH CDR1)
GFTFSSYAMS

SEQ ID NO: 12 (F9-VH CDR2)
AISGSGGSTYYADSVKG

SEQ ID NO: 13 (F9-VH CDR3)
AGYSLFDY

SEQ ID NO: 14 (F9-VL CDR1)
RASQSVSSSYLA

SEQ ID NO: 15 (F9-VL CDR2)
GASSRAT

SEQ ID NO: 16 (F9-VL CDR3)
QQDQGMPLT

The invention claimed is:

1. An antibody molecule that binds collagen, wherein the antibody molecule comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
   HCDR3 has the amino acid sequence shown in SEQ ID NO: 5;
   LCDR3 has the amino acid sequence shown in SEQ ID NO: 8;
   HCDR1 has the amino acid sequence shown in SEQ ID NO: 3,
   HCDR2 has the amino acid sequence shown in SEQ ID NO: 4,
   LCDR1 has the amino acid sequence shown in SEQ ID NO: 6, and
   LCDR2 has the amino acid sequence shown in SEQ ID NO: 7.

2. The antibody molecule according to claim 1, wherein the VH domain has the amino acid sequence shown in SEQ ID NO: 1, and the VL domain has the amino acid sequence shown in SEQ ID NO: 2.

3. An antibody molecule that binds collagen, wherein the antibody molecule comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
   HCDR3 has the amino acid sequence shown in SEQ ID NO: 13;
   LCDR3 has the amino acid sequence shown in SEQ ID NO: 16;
   HCDR1 has the amino acid sequence shown in SEQ ID NO: 11,
   HCDR2 has the amino acid sequence shown in SEQ ID NO: 12,
   LCDR1 has the amino acid sequence shown in SEQ ID NO: 14, and
   LCDR2 has the amino acid sequence shown in SEQ ID NO: 15.

4. The antibody molecule according to claim 3, wherein the VH domain has the amino acid sequence shown in SEQ ID NO: 9, and the VL domain has the amino acid sequence shown in SEQ ID NO: 10.

5. The antibody molecule according to claim 1, wherein the antibody molecule is or comprises a single chain Fv (scFv), is a small immunoprotein (SIP), is a diabody, or is an IgG molecule.

6. A conjugate comprising an antibody molecule according to claim 1 and a biocidal molecule, a cytotoxic molecule, an anti-inflammatory agent or a radioisotope.

7. The conjugate according to claim 6, wherein the biocidal molecule, or cytotoxic molecule, or anti-inflammatory agent is a cytokine.

8. The conjugate according to claim 1, wherein the conjugate is a fusion protein comprising the antibody molecule and a biocidal molecule, cytotoxic molecule, anti-inflammatory agent, or cytokine.

9. A conjugate comprising an antibody molecule according to claim 1 and a detectable label.

10. The antibody molecule according to claim 3, wherein the antibody molecule is or comprises a single chain Fv (scFv), is a small immunoprotein (SIP), is a diabody, or is an IgG molecule.

11. A conjugate comprising an antibody molecule according to claim 3 and a biocidal molecule, a cytotoxic molecule, an anti-inflammatory agent or a radioisotope.

12. A conjugate comprising an antibody molecule according to claim 3 and a detectable label.

13. A method of delivering a biocidal molecule, a cytotoxic molecule, an anti-inflammatory agent or a radioisotope to sites of osteoarthritis in a patient comprising administering to the patient a conjugate according to claim 6.

14. The method according to claim 13, wherein the molecule is an anti-inflammatory agent.

15. A method of delivering a biocidal molecule, a cytotoxic molecule, an anti-inflammatory agent or a radioisotope to sites of osteoarthritis in a patient comprising administering to the patient a conjugate according to claim 11.

* * * * *

SEQUENCE LISTING

<160> NUMBER OF SEQ ID NOS: 16

<210> SEQ ID NO 1
<211> LENGTH: 116
<212> TYPE: PRT
<213> ORGANISM: Artificial sequence
<220> FEATURE:
<223> OTHER INFORMATION: Synthetic amino acid sequence of antibody
      C11 - VH

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Gln Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Ala Ala Phe Asp Tyr Trp Gly Gln Gly Thr Leu Val
            100                 105                 110

Thr Val Ser Ser
        115

<210> SEQ ID NO 2
<211> LENGTH: 108
<212> TYPE: PRT
<213> ORGANISM: Artificial sequence
<220> FEATURE:
<223> OTHER INFORMATION: Synthetic amino acid sequence of antibody
      C11 - VL

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu

```
                35                  40                  45
Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile Gly Phe Pro
                85                  90                  95

Gln Thr Phe Gly Gln Gly Thr Lys Val Glu Ile Lys
            100                 105

<210> SEQ ID NO 3
<211> LENGTH: 10
<212> TYPE: PRT
<213> ORGANISM: Artificial sequence
<220> FEATURE:
<223> OTHER INFORMATION: Synthetic amino acid sequence of antibody
      C11 - VH CDR1

<400> SEQUENCE: 3

Gly Phe Thr Phe Ser Ser Tyr Ala Met Ser
1               5                   10

<210> SEQ ID NO 4
<211> LENGTH: 17
<212> TYPE: PRT
<213> ORGANISM: Artificial sequence
<220> FEATURE:
<223> OTHER INFORMATION: Synthetic amino acid sequence of antibody
      C11 - VH CDR2

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 7
<212> TYPE: PRT
<213> ORGANISM: Artificial sequence
<220> FEATURE:
<223> OTHER INFORMATION: Synthetic amino acid sequence of antibody
      C11 - VH CDR3

<400> SEQUENCE: 5

Thr Leu Ala Ala Phe Asp Tyr
1               5

<210> SEQ ID NO 6
<211> LENGTH: 12
<212> TYPE: PRT
<213> ORGANISM: Artificial sequence
<220> FEATURE:
<223> OTHER INFORMATION: Synthetic amino acid sequence of antibody
      C11 - VL CDR1

<400> SEQUENCE: 6

Arg Ala Ser Gln Ser Val Ser Ser Ser Tyr Leu Ala
1               5                   10

<210> SEQ ID NO 7
<211> LENGTH: 7
<212> TYPE: PRT
<213> ORGANISM: Artificial sequence
<220> FEATURE:
<223> OTHER INFORMATION: Synthetic amino acid sequence of antibody
```

C11 - VL CDR2

<400> SEQUENCE: 7

Gly Ala Ser Ser Arg Ala Thr
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic amino acid sequence of antibody
      C11 - VL CDR3

<400> SEQUENCE: 8

Gln Gln Ala Ile Gly Phe Pro Gln Thr
1               5

<210> SEQ ID NO 9
<211> LENGTH: 117
<212> TYPE: PRT
<213> ORGANISM: Artificial sequence
<220> FEATURE:
<223> OTHER INFORMATION: Synthetic amino acid sequence of antibody
      F9 - VH

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Tyr Ser Leu Phe Asp Tyr Trp Gly Gln Gly Thr Leu
            100                 105                 110

Val Thr Val Ser Ser
        115

<210> SEQ ID NO 10
<211> LENGTH: 108
<212> TYPE: PRT
<213> ORGANISM: Artificial sequence
<220> FEATURE:
<223> OTHER INFORMATION: Synthetic amino acid sequence of antibody
      F9 - VL

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asp Gln Gly Met Pro
                 85                  90                  95

Leu Thr Phe Gly Gln Gly Thr Lys Val Glu Ile Lys
            100                 105

<210> SEQ ID NO 11
<211> LENGTH: 10
<212> TYPE: PRT
<213> ORGANISM: Artificial sequence
<220> FEATURE:
<223> OTHER INFORMATION: Synthetic amino acid sequence of antibody
      F9 - VH CDR1

<400> SEQUENCE: 11

Gly Phe Thr Phe Ser Ser Tyr Ala Met Ser
1               5                   10

<210> SEQ ID NO 12
<211> LENGTH: 17
<212> TYPE: PRT
<213> ORGANISM: Artificial sequence
<220> FEATURE:
<223> OTHER INFORMATION: Synthetic amino acid sequence of antibody
      F9 - VH CDR2

<400> SEQUENCE: 12

Ala Ile Ser Gly Ser Gly Gly Ser Thr Tyr Tyr Ala Asp Ser Val Lys
1               5                   10                  15

Gly

<210> SEQ ID NO 13
<211> LENGTH: 8
<212> TYPE: PRT
<213> ORGANISM: Artificial sequence
<220> FEATURE:
<223> OTHER INFORMATION: Synthetic amino acid sequence of antibody
      F9 - VH CDR3

<400> SEQUENCE: 13

Ala Gly Tyr Ser Leu Phe Asp Tyr
1               5

<210> SEQ ID NO 14
<211> LENGTH: 12
<212> TYPE: PRT
<213> ORGANISM: Artificial sequence
<220> FEATURE:
<223> OTHER INFORMATION: Synthetic amino acid sequence of antibody
      F9 - VL CDR1

<400> SEQUENCE: 14

Arg Ala Ser Gln Ser Val Ser Ser Ser Tyr Leu Ala
1               5                   10

<210> SEQ ID NO 15
<211> LENGTH: 7
<212> TYPE: PRT
<213> ORGANISM: Artificial sequence
<220> FEATURE:
<223> OTHER INFORMATION: Synthetic amino acid sequence of antibody
      F9 - VL CDR2

<400> SEQUENCE: 15

Gly Ala Ser Ser Arg Ala Thr
```

```
<210> SEQ ID NO 16
<211> LENGTH: 9
<212> TYPE: PRT
<213> ORGANISM: Artificial sequence
<220> FEATURE:
<223> OTHER INFORMATION: Synthetic amino acid sequence of antibody
      F9 - VL CDR3

<400> SEQUENCE: 16

Gln Gln Asp Gln Gly Met Pro Leu Thr
1               5
```